United States Patent
Gundlack et al.

(10) Patent No.: US 12,354,737 B2
(45) Date of Patent: Jul. 8, 2025

(54) METHOD FOR DETERMINING A MODEL OF AN EXTREMITY, COMPUTER-READABLE STORAGE MEDIUM AND SYSTEM

(71) Applicant: Ottobock SE & Co. KGaA, Duderstadt (DE)

(72) Inventors: Felix Gundlack, Munich (DE); Max Thalmeier, Munich (DE); Khoi Lam, Munich (DE)

(73) Assignee: Ottobock SE & Co. KGaA, Duderstadt (DE)

( * ) Notice: Subject to any disclaimer, the term of this patent is extended or adjusted under 35 U.S.C. 154(b) by 192 days.

(21) Appl. No.: 17/424,564

(22) PCT Filed: Jan. 8, 2020

(86) PCT No.: PCT/EP2020/050258
§ 371 (c)(1),
(2) Date: Jul. 21, 2021

(87) PCT Pub. No.: WO2020/151944
PCT Pub. Date: Jul. 30, 2020

(65) Prior Publication Data
US 2022/0076817 A1    Mar. 10, 2022

(30) Foreign Application Priority Data
Jan. 21, 2019   (DE) .................... 10 2019 101 370.4

(51) Int. Cl.
*G16H 40/63*    (2018.01)
*G16H 30/20*    (2018.01)

(52) U.S. Cl.
CPC ............. *G16H 40/63* (2018.01); *G16H 30/20* (2018.01)

(58) Field of Classification Search
USPC ............................................................ 705/2
See application file for complete search history.

(56) References Cited

U.S. PATENT DOCUMENTS

| 8,644,568 B1 * | 2/2014 | Hoffmann | G16H 50/50 |
| | | | 382/128 |
| 2005/0119777 A1 | 6/2005 | Arbogast et al. | |

(Continued)

FOREIGN PATENT DOCUMENTS

| DE | 1480480 B1 | 11/1969 |
| DE | 4041105 A1 | 6/1992 |

(Continued)

OTHER PUBLICATIONS

Oosterwaal et al. (2011). Generation of subject-specific, dynamic, multisegment ankle and foot models to improve orthotic design: a feasibility study. BMC Musculoskeletal Disorders, 12, 256. doi:http://dx.doi.org/10.11 (Year: 2011).*

(Continued)

*Primary Examiner* — Bennett Stephen Erickson
(74) *Attorney, Agent, or Firm* — Goodwin Procter LLP

(57) ABSTRACT

The invention relates to a method for determining a model of an extremity, for providing an individually designed orthosis or prosthesis, the method comprising a step of displaying at least one option for data input by a user, in particular in the form of a patient questionnaire. In a further step, the determination of at least one patient-specific input parameter takes place on the basis of the data input. In one step, the creation of at least one raw model takes place using the at least one input parameter. In a further step, the ascertaining of at least one measured parameter of the raw model and, according to one step, the visualizing, in particular displaying, of the raw model and the at least one measured parameter takes place. Furthermore, the invention (Continued)

relates to a computer-readable storage medium and also a system.

9 Claims, 1 Drawing Sheet

(56) References Cited

U.S. PATENT DOCUMENTS

| | | | | |
|---|---|---|---|---|
| 2010/0106475 | A1* | 4/2010 | Smith | G16H 50/50 703/11 |
| 2012/0078254 | A1* | 3/2012 | Ashby | A61B 17/1764 606/87 |
| 2014/0003695 | A1* | 1/2014 | Dean | A61B 5/1075 382/131 |
| 2017/0061375 | A1* | 3/2017 | Laster | G16H 20/40 |
| 2017/0360578 | A1 | 12/2017 | Shin et al. | |
| 2019/0172570 | A1* | 6/2019 | Popescu | G16H 30/20 |

FOREIGN PATENT DOCUMENTS

| | | |
|---|---|---|
| DE | 102015004319 A1 | 10/2016 |
| EP | 3197124 A1 | 7/2017 |

OTHER PUBLICATIONS

Colombo et al.: "A digital patient for computer-aided prosthesis design"; Interface Focus3: 20120082.; 2013; 13 pages.
German Patent and Trademark Office; Office Action for related application DE 10 2019 101 370.4; Sep. 20, 2019; 13 pages.
Patent Cooperation Treaty: International Search Report and Written Opinion for PCT/EP2020/050258; Cornelia Schulze; Mar. 10, 2020; 17 pages.
Patent Cooperation Treaty: Written Opinion of the International Searching Authority for PCT/EP2020/050258; Nora Lindner; Jul. 29, 2021 ; 7 pages.

* cited by examiner

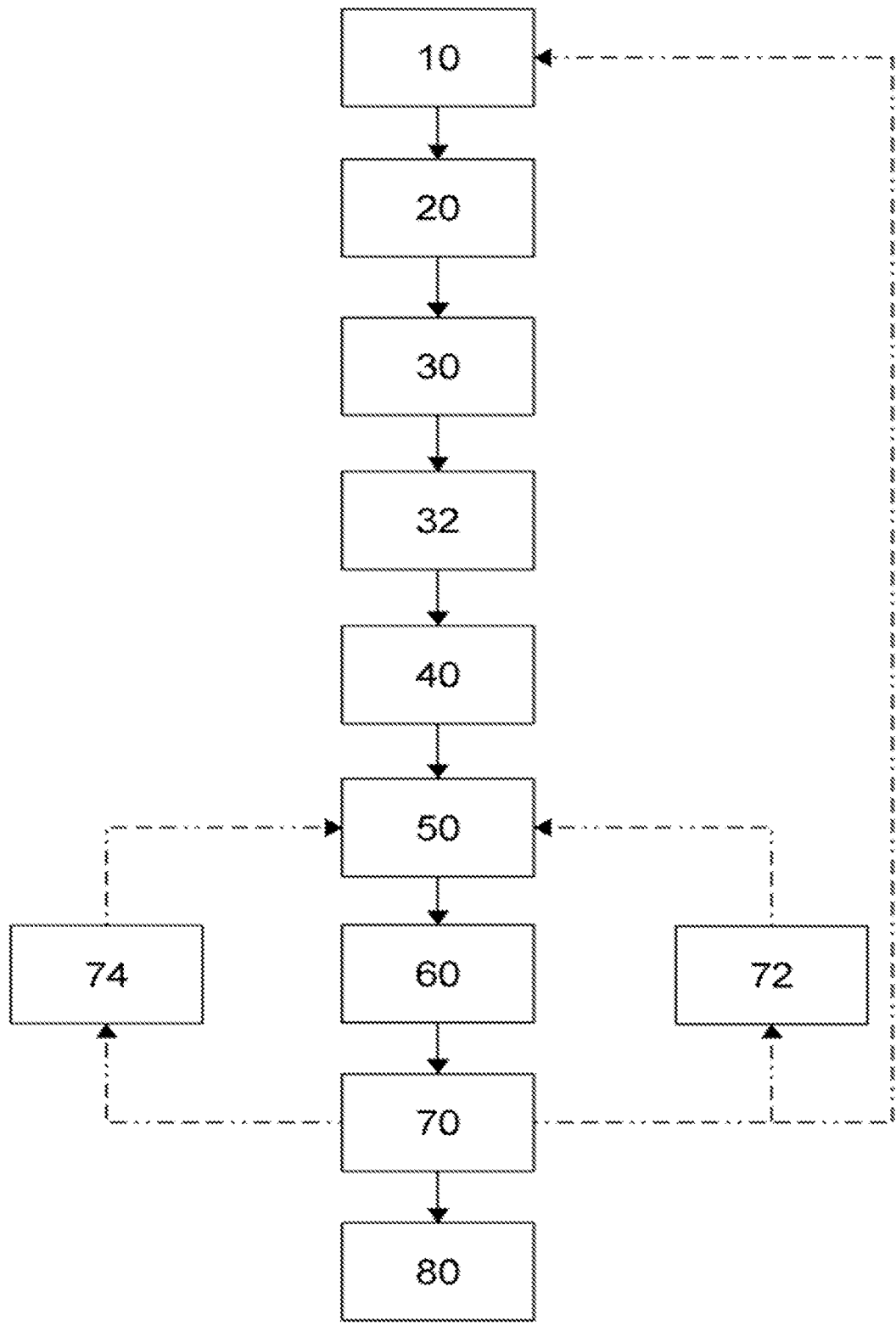

METHOD FOR DETERMINING A MODEL OF AN EXTREMITY, COMPUTER-READABLE STORAGE MEDIUM AND SYSTEM

CROSS-REFERENCE TO RELATED APPLICATIONS

This application is a U.S. National Phase application submitted under 35 U.S.C. § 371 of Patent Cooperation Treaty application serial no. PCT/EP2020/050258, filed Jan. 8, 2020, and entitled METHOD FOR DETERMINING A MODEL OF AN EXTREMITY, COMPUTER-READABLE STORAGE MEDIUM AND SYSTEM, which application claims priority to German patent application serial no. 10 2019 101 370.4, filed Jan. 21, 2019, and entitled METHOD FOR DETERMINING A MODEL OF AN EXTREMITY, COMPUTER-READABLE STORAGE MEDIUM AND SYSTEM.

Patent Cooperation Treaty application serial no. PCT/EP2020/050258, published as WO 2020/151944 A1, and German patent application serial no. 10 2019 101 370.4, are incorporated herein by reference.

TECHNICAL FIELD

The invention relates to a method for determining a model of an extremity, in particular for providing an individually designed orthosis or prosthesis.

BACKGROUND

Pre-assembled orthoses and/or prostheses provide a comparatively inexpensive way of providing a replacement in both aesthetic and functional respects to patients with amputated or injured extremities. However, due to the limited possibilities for conforming to the patient's anatomy, these standard solutions can present significant challenges in respect of aesthetics and wearing comfort.

However, the individual modeling, production and adaptation of orthoses or prostheses, including covers or shells, to achieve an aesthetically pleasing extremity, is a laborious and time-consuming process.

For such a patient-specific solution, it is possible to capture the analogous, healthy extremity for the reconstruction of the injured or amputated extremity by means of a three-dimensional scan. In this way, significant size dimensions for a patient-specific adaptation of the orthosis or the prosthesis can already be determined. Conventionally however, significantly simpler methods in the form of manual measurements are used for this purpose, whereby relevant anatomical measurements are acquired on the basis of so-called dimensional drawings.

To do this, the patient must undergo a 3D-scan by a doctor or an orthopedic specialist. In addition, the correct seating of the device must be adjusted and ensured on site. Furthermore, in bilaterally amputated persons, a comparable, analogue extremity, which would make the acquisition by means of a 3D-scan possible in the first place, is lacking.

SUMMARY

It is an object of the invention to provide a method that allows the determination of a model of an extremity, in particular for the provision of an individually designed orthosis or prosthesis, in a simple and efficient manner, without the need to capture an analogous, comparable anatomical structure, wherein a patient-specific adaptation of the model and the resulting orthosis or prosthesis is also ensured. It is a further object of the invention to provide a storage medium and a system.

According to the present invention, a method for determining a model of an extremity, in particular for providing an individually designed orthosis or prosthesis, is provided with the following steps:

a) displaying at least one option for data input by a user, in particular in the form of a patient questionnaire;
b) determining at least one patient-specific input parameter on the basis of the data input;
c) generating at least one raw model, in particular the raw model of an extremity, using the at least one input parameter;
d) ascertaining at least one measurement parameter of the raw model;
e) visualizing the raw model and/or the at least one measured parameter.

The invention is based upon the basic idea of determining a model and/or a raw model of an extremity of a patient on the basis of information provided by the user himself/herself. In particular, it is provided that the patient-individual or patient-specific information is provided by the respective patient or user.

Thus, it is possible to provide at least one raw model without performing a 3D scan or other measurement method. The raw model is based upon information that a patient himself/herself enters and that describes his/her physical constitution. On the basis of the raw model, an individualized orthosis or prosthesis can then be produced.

In the context of the invention, the raw model can relate to a single extremity or to the entire body of a patient to depict suitably the proportions of the extremities and the entire body.

A user, in the context of the present invention, should be understood to be a patient, a treating physician or a certified prosthetist orthotist. Thus, the data input can be made directly by the patient himself/herself or by another person assigned to treat the patient.

In particular, it can be provided that a questionnaire is shown to the patient providing appropriate options for data input. This allows the patient to enter general information himself/herself in order to gather data for the at least one raw model to be determined. No laborious generation of anatomical data on the basis of a 3D-scan or the like is necessary. Rather, it is conceivable that the user is presented with general questions regarding the person himself/herself and his/her physical constitution on the basis of which, in particular, basic anatomical dimensions for a prosthesis or an orthosis can be derived.

Alternatively, it is conceivable that the user provides an image of an extremity and/or an anatomy, or of his/her body for data input, corresponding input parameters being ascertainable from the provided image.

At least one patient-specific input parameter that provides an anatomical size dimension is ascertained on the basis of the at least one user data input. Based on the input of, for example, the age, sex, height, shoe size, and/or weight, basic size dimensions, for example, of a lower leg extremity can be determined as input parameters.

Basic structural dimensions of the raw model can be derived from the at least one input parameter, for example in order to model a patient's extremity. The raw model is used for the production of the orthosis or prosthesis. The raw model, which can be generated solely on the basis of the input parameters, represents, in particular, a first approximation of the relevant extremity for which an individualized orthosis or a prosthesis is to be generated. It is provided, in particular, that this first approximation of the raw model is further individualized on the basis purely of the input parameters.

By ascertaining at least one measured parameter on the raw model, parameters for the orthosis or prosthesis can be determined. Basic dimensions or measurements can be determined and clarified for the user.

Furthermore, it is contemplated that the raw model will be visualized, in particular displayed, after generation. In this way, a pictorial, preferably spatial impression of the result of the data input can be provided and imparted to the user, in particular to the patient.

According to a preferred embodiment, the visualization of the raw model takes place in the form of the display of an avatar. Thus, the user can be provided with an impression of the result of the data input and the input parameters ascertained therefrom.

In the context of the present invention, an avatar should be understood to be a preferably two- or three-dimensional representation of the raw model for illustration for the user.

In a further preferred embodiment, the method comprises the steps, in particular before or after reception of the at least one input parameter, of:
g1) displaying a number of images or three-dimensional representations, in particular on the basis of the one or more avatars;
g2) receiving a data input in the form of a selection by the user of at least one image and/or at least one representation,
g3) determining at least one shape parameter on the basis of the selection of the at least one image and/or the at least one representation,
wherein the at least one raw model or at least one of the raw models is/are generated using the at least one input parameter and/or the at least one shape parameter.

In the context of the present invention, a shape parameter can be used, for example, to determine muscle volumes or muscle proportions of the body weight, to specify the definedness of individual tissue parts and/or of the upper body or the lower body, or the like. Thus, the approximate external appearance of the patient's extremity or body structure can be determined by the user on the basis of the at least one shape parameter.

Furthermore, it is possible according to the invention that the step of displaying at least one option for data input by the user comprises displaying a number of images, wherein the data input comprises selecting at least one of the displayed images. The determination of the shape parameters and the input parameters can thus be made in a similar or identical manner, in particular through the display and selection of images.

In particular, it is provided that the at least one shape parameter is ascertained on the basis of the selection from a number of images through a corresponding data input by the user. Thus, the images can be used to illustrate various examples of a patient's body structure. The shape parameters can thus be determined or derived from the selection of one or more of the number of images. A basic definition of the patient's body structure is easily providable.

In one embodiment, an iterative determination and/or refinement of the raw model takes place. For example, at least the steps g1) to g3) can be performed multiple times in order to generate and/or refine a raw model iteratively using the at least one input parameter and the at least one shape parameter.

In a further embodiment the method has the steps of:
ascertaining at least one statistically-based characteristic parameter from an anatomical database using the at least one input parameter and/or a/the at least one shape parameter,
using the characteristic parameter to generate the raw model.

To ascertain the at least one statistically-based characteristic parameter, an anatomical database with a large number of example cases of anatomical values of different patients can be used. If the patient-specific input parameters or shape parameters are used as a reference, further dimensions for the raw model can be provided by statistical analysis of the anatomical data sets which form the basis of the database. The statistically-based characteristic parameters to be ascertained can therein be based upon, for example, anthropological relationships between individual dimensions of a patient's extremity.

Using such an anatomical database to ascertain statistically-based characteristic parameters, statistically ascertainable relationships of anatomical dimensions can be incorporated into the configuration of the raw model.

According to a preferred embodiment, the method comprises the step of:
modifying the raw model on the basis of the at least one measured parameter, in particular to optimize the outer contour.

Using the at least one measured parameter, the user can undertake an adaptation of the raw model himself/herself. For example, the outer contour of the raw model can be optimized on the basis of the input parameters, measured parameters, shape parameters and/or characteristic parameters already considered.

An individual modification of the raw model is available on the basis of the measured parameters to be able to determine a patient-specific raw model.

According to one embodiment, it is provided that the ascertainment of the at least one measured parameter of the raw model takes place through a linking of the raw model to at least two reference points and/or at least one reference plane and a dimensioning of a distance between the reference points and/or a common geometry.

The raw model can be defined in particular by areas and/or volumes. In this way, the raw model presents a modeling of anatomical surface structures, preferably with anatomically prominent node points and/or reference points.

The outer shell provided on the basis of the raw model is linkable to a preferably freely selectable reference plane and/or the reference plane can extend through the surfaces and/or volumes of the raw model such that the reference plane intersects, and/or overlaps with, the raw model. In this way, the raw model and the reference plane form a common surface or a common edge shape.

The measured parameter can accordingly be determinable on the basis of a common edge shape, for example in terms of a circumference of an extremity cross-section, or on the basis of a (volume) surface area for determining the extremity cross-sectional volume at a specific position of the extremity, such as the calf musculature. Further, it is possible, for example, to capture a distance between two reference points as a measure for an extremity.

According to a further preferred embodiment, the at least one reference plane is determined by means of three predetermined reference points on the raw model or by means of at least one predetermined reference point on the raw model and a predetermined orientation.

In particular, the reference plane can be defined and/or predetermined on the basis of anatomically prominent reference points. Thus, articulation surfaces, end points of bone structures, or the like, can serve to establish the reference plane. It is also possible to define a reference plane on the basis of the progression through a single reference point as well as a pre-determined orientation, preferably in the sense of a normal vector.

According to a further embodiment, the at least one input parameter describes an extremity, in particular the raw model describes a surface or a volume of the extremity, and/or has at least one patient-specific data input to demographic information and/or pathological information.

Pathological data and/or information can refer to disease patterns such as a club foot, an immobilization of the ankles, particularly osteoarthritis, osteoarthropathy, pseudarthroses, osteonecroses and arthrodeses, a foot drop, a fibular ligament rupture, a flaccid paralysis due to, for example, cerebral paresis, a scoliosis, a drop foot, a splay foot, a degree of amputation of an extremity or the like.

The input parameter can be regarded as a descriptive indication of the extremity or of the personal patient information. For example, an input parameter can specify the type of extremity and can also determine general patient information. The input parameters thus represent the general basis for the raw model, wherein a further-reaching specification of the raw model can be carried out, in particular on the basis of the measurement parameters, the shape parameters and/or the characteristic parameters.

The different types of parameters can differ, in particular with respect to their modifiability, as well as the procedure for determining them. Thus, the statistically-based characteristic parameters are not directly modifiable by the user. On the other hand, the ascertained measured parameters can be adjustable by the user, similarly to the shape parameters, by corresponding selection from the number of images.

Furthermore, it can be provided that the method comprises the steps of:
 determining, by an authorized user, at least one anatomical parameter to be individually defined;
 modifying the raw model using the at least one anatomical parameter.

In the context of the present invention, a treating physician or orthopedic physician or other person with sufficient technical expertise is preferably intended as an authorized user. In particular, a patient is not to be understood as an authorized user in the context of the invention.

Thus, it is possible for essential and, in particular, critical anatomical parameters of the raw model to be adapted by a physician and/or orthopedic physician on the basis of the definition of anatomical parameters. Thus, basic and/or very specific changes of the dimensions and measurements can be made to the raw model, if necessary. This can be necessary, for example from a medical or orthopedic point of view, if the raw model inadequately reflects the anatomy of the patient, in particular on the basis of the input parameters. In particular, parameters of the raw model that are critical for the later implementation of an orthosis or prosthesis from a safety or medical point of view can be captured in the form of anatomical parameters.

Furthermore, the method can be provided as an iterative method, wherein the steps from the display of at least one option for data input through to the visualization of the at least one generated raw model repeat multiple times for iteratively determining the model of an extremity.

In particular, the at least one raw model can be optimized and refined in iterative form in order to allow a stepwise approximation to the patient-specific anatomy. For this purpose, the method according to the invention can be run through multiple times, wherein the steps from the data input to the visualization preferably alternate and/or repeat. In this way, a step-wise optimization can be enabled for the user to gradually optimize the at least one raw model.

Particularly preferably, a plurality of raw models can be generated and displayed, the number of raw models being reduced step-wise within the iterative process and approximated to the patient-specific anatomy so that a patient-specific individualized raw model is achievable.

According to a further preferred embodiment, the method comprises the step of:
 controlling a production plant using the raw model which is configured for producing an individually designed orthosis or prosthesis.

Accordingly, the individualized raw model can be used directly for implementation or production of an individualized orthosis or prosthesis, preferably by means of an additive production method, in particular a 3D-printing process, a (computer-controlled) milling method, or the like. The individualized orthosis or prosthesis can be made of a plastics material, a foam material, polymers, in particular silicone, a metal, or the like. In this regard, the patient-specific raw model represents the patient's individual extremity for which the orthosis or prosthesis is to be produced.

In a subsidiary aspect of the invention, there is provided a computer-readable storage medium containing instructions to cause at least one processor to implement a method according to one of the preceding claims when the instructions are executed by the at least one processor.

According to a further subsidiary aspect, there is provided a system comprising:
 at least one server with at least one computer unit and at least one storage unit, in particular a storage medium according to the invention,
 at least one mobile terminal device,
 wherein the system is preferably configured to implement the method according to the present invention.

In particular, the mobile terminal device can be provided for data input by the user. Thus, the user can provide, in a simple, efficient manner, necessary data for determining the raw model. Furthermore, a visualization can be displayed directly on the mobile terminal device, in particular by displaying an avatar of the raw model.

BRIEF DESCRIPTION OF THE DRAWINGS

The invention will now be described in greater detail by reference to exemplary embodiments. In the drawing:
 is a schematic flow diagram of an exemplary embodiment of the method according to the invention.

DETAILED DESCRIPTION

FIG. 1 shows an exemplary embodiment of a method for determining a model of an extremity in the form of a flowchart.

In a first step, data input 10 is performed by a user. Herein, the user can be a physician, a certified prosthetist orthotist, or preferably, the patient himself/herself. No special authorization of the user is required. Rather, general information about the patient or the physical constitution of the patient is requested by means of the data input. Demographic and/or pathological information can thus be requested or entered in this way.

In particular, it is provided that options for entering data are displayed to the user in the form of a questionnaire. Thus, data such as the patient's age, height, shoe size or sex can be received from the user.

In a next step, various input parameters 20 are determined from the input information or the data input. These input parameters relate to the most basic properties of at least one raw model to be generated. The input parameters can in particular be extracted from the sum of the entered data, such as the height in combination with the sex and the weight.

In a further step, a display 30 of a number of images takes place, which can preferably be on the basis of a selection from an anatomical database. These images can include the upper body or lower body and/or various extremities as well as different forms of these extremities. Thus, different body or extremity forms, among other things, in terms of weight and body fat content can be presented to the user for selection. In his/her selection of the images, the user can be guided by the structure of the relevant extremity known to him/her. A direct comparison with the second analogous extremity, as in the case of a 3D-scan, is not necessary. Rather, a free choice can also be made for bilaterally amputated patients.

Following the selection of at least one image 30, on the basis thereof, various shape parameters are determined and/or the selection of shape parameters which specify more precisely and/or individualize the outer contour of the at least one raw model more precisely is restricted. Thus, the selection of the images for the definition of the extremity, in particular for the aesthetic definition of the extremity, can be taken into account for the at least one raw model to be produced. The at least one raw model is thus more precisely specifiable.

Preferably, a plurality of raw models is continuously reduced as part of an iterative procedure and approximated to the patient-specific anatomy to obtain a patient-specific raw model.

In a further step, the ascertainment of statistically-based characteristic parameters 40 is carried out. In particular, for this purpose, an anatomical database can be used which can contain a large number of anatomical dimensions for different patients in order to provide a socially well-founded, anthropological data basis. In this way, further dimensions in the form of characteristic parameters can be determined in a statistical manner on the basis of the input parameters already ascertained as well as the shape parameters, so that the raw model can be further specified in its individual dimensioning and size measurements.

Alternatively, the determination of statistically-based characteristic parameters 40 can be determined directly in combination with the determination of the input parameters and/or the shape parameters.

According to the exemplary embodiment of FIG. 1, in the subsequent step, the generation of a raw model 50 takes place on the basis of the input parameters, the shape parameters and the key parameters. On the basis of the input of the input parameters, preferably in the form of a questionnaire, as well as the shape parameters, preferably in the sense of selecting from a number of images, a simplified and rapid provision of the raw model is possible.

A time-consuming 3D-scan, or medical or orthopedic examinations are not necessary. Rather, the patient himself/herself or another third party as the user can also provide the necessary information for generating a raw model.

In one step, it is provided within the scope of the invention for at least one measured parameter to be determined and ascertained 60 by the user. Thus, for example, an outer circumference and/or a cross-sectional volume along the calf musculature can be determined.

Subsequently, the visualization of the raw model 70, preferably in the form of the display or pictorial representation of the raw model, takes place. In particular, it is provided that the raw model is displayed as an avatar so that the user receives a pictorial or spatial representation of the raw model. Furthermore, the specified measured parameter 60 can be displayed together with the avatar. Thus, the user can compare the aesthetic appearance and the dimensioning with the extremity to be treated and/or replaced.

After the display of the raw model 70, it can be possible for any user to adapt 72 the ascertained measurement parameters 60 along the contour of the raw model. The raw model can thus also be adaptable directly for a patient, at least to a limited extent.

By contrast, a determination and adaptation of anatomical parameters 74 by an authorized user can take place. An authorized user should be understood, in particular, to be a physician or orthopedic physician with the necessary background knowledge.

The determination and/or adaptation of anatomical parameters 74 can offer the authorized user more extensive possibilities for individualizing and specific adaption of the raw model, wherein the measured parameters can only provide limited capabilities for any user to revise the generated raw model on the basis, in particular, of the input parameters, the shape parameters, and the characteristic parameters.

For example, essential dimensions of the raw model can be modifiable on the basis of the anatomical parameters, in order to optimize, for example, the correct fit of the orthosis or prosthesis in joint regions or the like. In particular, on the basis of the anatomical parameters, the existing data and/or dimensions from the input parameters, the shape parameters and/or the characteristic parameters can be overwriteable.

As optional method possibilities, the adaptation of the measured parameters 72 as well as the anatomical parameters 74 are represented dashed in FIG. 1.

Following the optional modification of the anatomical parameters 74 and/or the measured parameters 72, a new generation 50 and visualization 70 of the raw model takes place.

Thus, the new parameters can be checked in the raw model that is shown, preferably displayed as an avatar. Naturally, a direct spontaneous regeneration and revisualization of the raw model after modification of the measured parameters 72 and/or the anatomical parameters 74 is conceivable, so that the user and/or the authorized user can directly observe or observe the change made in the displayed avatar.

Modification of the raw model after visualization 70 on the basis of the measured parameters 72 and/or the anatomical parameters 74 thus enables extensive individualizability on the basis of the generated and illustrated raw model.

Furthermore, the method according to FIG. 1 can be configured as an iterative method (indicated dashed in FIG. 1). Thus, after the visualization 70 of the at least one raw model, it is possible to perform a new data input 10 to further determine the at least one raw model.

In particular, the steps from data input 10 to visualization 70 can be re-executable or executable in direct exchange with one another. Alternatively, for example, the display of images 30 and the determination of the shape parameters 32 can also be alternatable with the visualization 70 of the at least one raw model.

In that the method according to FIG. 1 is run through multiple times and in an iterative form, an initial plurality of raw models can be approximated step-wise to the patient-specific anatomy and the number of raw models specifically reduced in order to arrive at the display of a best possible individualized raw model.

In particular, the plurality of raw models can present to the user, preferably on the basis of an anatomical database, a continuously more precisely specifying selection of anatomies, so that the user arrives, on the basis of iterative data input, at an optimized approximation to the desired anatomy and/or extremity. The display of a plurality of raw models can be understood herein as a selection of different alternatives on the basis of the information and/or data fundamentals provided up to that time.

Provided that the raw model 70 shown is sufficiently individualized and dimensioned, the transfer of the patient-specific raw model to a production plant 80 takes place. In particular, the production plant can be controlled by means of the raw model in such a way that an individually designed prosthesis or an associated, individually designed orthosis is produced on the basis of the raw model.

In particular, it is provided that the production plant is configured as a 3D-printing system or as a milling system for additive or subtractive production of the orthosis and/or prosthesis to be provided.

Thus, on the basis of the production plant, the conversion of the individualized raw model of a patient's extremity into an orthosis or prosthesis is possible without the need for a time-consuming 3D-scan or further examinations. Rather, the raw model is preferably sufficiently determinable by the patient's data input as the basis for the orthosis and/or prosthesis to be formed.

In summary, a possibility for simple and efficient generation of a raw model can be provided on the basis of the present invention in order, on this basis, to produce a specifically adapted orthosis or prosthesis, preferably in a 3D-printing method or a milling method.

REFERENCE NUMERALS

10 Data input by the user
20 Determination of the input parameters
30 Display of a number of images
32 Determination of shape parameters
40 Ascertainment of statistically-based characteristic parameters
50 Generation of a raw model
60 Determination of measurement parameters
70 Visualization of the raw model
72 Adaptation of measurement parameters
74 Determination/adaptation of anatomical parameters
80 Control of the production plant

The invention claimed is:

1. A method for determining a model of an extremity for providing an orthosis or prosthesis for that extremity, having the following steps:
   a) displaying at least one option for data input by a user in the form of a patient questionnaire;
   b) providing a data input by a user;
   c) determining at least one patient-specific input parameter on the basis of the data input;
   d) accessing an anatomical database storing a plurality of anatomical data sets, which anatomical data sets are associated with example cases of anatomical values of different patients;
   e) determining reference dimensions of a raw model of the extremity for which the orthosis or prosthesis is to be generated with the use of the anatomical data sets and the determined at least one patient-specific input parameter;
   f) ascertaining at least one statistically-based characteristic parameter from the anatomical database using the determined at least one patient-specific input parameter as a reference;
   g) generating the raw model of the extremity using the ascertained at least one statistically-based characteristic parameter;
   h) incorporating statistically ascertainable relationships of anatomical dimensions into a configuration of the raw model;
   i) ascertaining a measurement parameter of the raw model, the measurement parameter representing a measurement of a distance between two points on the raw model, or a volume, an area, or a contour in the raw model;
   j) displaying the raw model and the measurement parameter;
   k) receiving an adjustment of the measurement parameter;
   l) modifying the raw model on the basis of the ascertained measurement parameter;
   m) iteratively performing steps j) through l) to further adjust the measurement parameter and modify the raw model on the basis of the further adjusted measurement parameter until a stopping condition is met to generate an individualized model of the orthosis or prosthesis; and
   n) generating and transmitting instructions for a 3D-printing system or a milling system of a production plant, the instructions causing the 3D-printing system to additively manufacture, or causing the milling system to subtractively manufacture, a shape corresponding to the individual model to create the orthosis or prosthesis from the individualized model.

2. The method according to claim 1, wherein displaying the raw model comprises displaying an avatar or a plurality of avatars.

3. The method according to claim 1, wherein ascertaining the measurement parameter comprises:
   i1) displaying at least one image or three-dimensional representation,
   i2) receiving a data input in the form of a selection by the user of at least one image or at least one three-dimensional representation, and
   i3) determining at least one shape parameter on the basis of the selection of the at least one image or the at least one three-dimensional representation; and
   wherein generating the raw model comprises using the at least one input parameter and the at least one shape parameter.

4. The method according to claim 3, wherein the steps i1) to i3) are performed multiple times in order iteratively to generate or refine the raw model using the at least one input parameter and the at least one shape parameter.

5. The method according to claim 1, further comprising modifying the raw model on the basis of the at least one measured parameter to optimize an outer contour.

6. The method according to claim 1, wherein-ascertaining the at least one measured parameter of the raw model comprises:

determining a reference plane of the raw model that corresponds to, intersects, or overlaps with the raw model such that the raw model and the reference plane form a common geometry;

linking the raw model to at least one reference point in the reference plane and a dimensioning of a distance between the at least one reference plane and the common geometry.

7. The method according to claim 6, wherein the reference plane is determined based on three predetermined reference points on the raw model, or is determined by at least one predetermined reference point on the raw model and a predetermined orientation.

8. The method according to claim 1, wherein the at least one patient-specific input parameter describes an extremity and the at least one raw model describes a surface or a volume of the extremity, or the at least one patient-specific input parameter has at least one patient-specific data input to a demographic information or pathological information.

9. A non-transitory computer-readable storage medium containing instructions for causing at least one processor to, when the instructions are executed by the at least one processor:

a) display at least one option for data input by a user in the form of a patient questionnaire;
b) provide a data input by a user;
c) determine at least one patient-specific input parameter on the basis of the data input;
d) access an anatomical database storing a plurality of anatomical data sets, which anatomical data sets are associated with example cases of anatomical values of different patients;
e) determine reference dimensions of a raw model of the extremity for which the orthosis or prosthesis is to be generated with the use of the anatomical data sets and the determined at least one patient-specific input parameter;
f) ascertain at least one statistically-based characteristic parameter from the anatomical database using the determined at least one patient-specific input parameter as a reference;
g) generate the raw model of the extremity using the ascertained at least one statistically-based characteristic parameter;
h) incorporate statistically ascertainable relationships of anatomical dimensions into a configuration of the raw model;
i) ascertain a measurement parameter of the raw model, the measurement parameter representing a measurement of a distance between two points on the raw model, or a volume, an area, or a contour in the raw model;
j) display the raw model and the measurement parameter;
k) receive an adjustment of the measurement parameter;
l) modify the raw model on the basis of the ascertained measurement parameter;
m) iteratively performing steps k) through l) to further adjust the measurement parameter and modify the raw model on the basis of the further adjusted measurement parameter until a stopping condition is met to generate an individualized model of the orthosis or prosthesis; and
n) generating and transmitting instructions for a 3D-printing system or a milling system of a production plant, the instructions causing the 3D-printing system to additively manufacture, or causing the milling system to subtractively manufacture, a shape corresponding to the individualized model to create the orthosis or prosthesis from the individualized model.

* * * * *